United States Patent
Radomsky et al.

(10) Patent No.: US 6,645,945 B1
(45) Date of Patent: *Nov. 11, 2003

(54) METHOD OF TREATING DISEASED, INJURED OR ABNORMAL CARTILAGE WITH HYALURONIC ACID AND GROWTH FACTORS

(75) Inventors: Michael Radomsky, San Diego, CA (US); Mohammad A. Heidaran, Los Gatos, CA (US)

(73) Assignee: DePuy Acromed, Inc., Raynham, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 28 days.

(21) Appl. No.: 09/298,539

(22) Filed: Apr. 22, 1999

Related U.S. Application Data

(63) Continuation-in-part of application No. 08/811,971, filed on Mar. 5, 1997, now Pat. No. 5,942,499, which is a continuation-in-part of application No. 08/611,690, filed on Mar. 5, 1996, now abandoned.

(51) Int. Cl.$^7$ .................. A61K 31/715; C08B 37/00
(52) U.S. Cl. .................. 514/54; 514/2; 514/62; 536/53; 530/350; 623/16
(58) Field of Search .................. 514/2, 54, 62; 536/53; 530/350; 623/16

(56) References Cited

U.S. PATENT DOCUMENTS

| | | | |
|---|---|---|---|
| 4,394,370 A | 7/1983 | Jeffries | 424/15 |
| 4,409,332 A | 10/1983 | Jeffries et al. | 435/188 |
| 4,472,840 A | 9/1984 | Jeffries | 3/1.9 |
| 5,013,714 A | 5/1991 | Lindstrom et al. | 514/4 |
| 5,030,457 A | 7/1991 | Ng et al. | 424/486 |
| 5,100,668 A | 3/1992 | Edelman et al. | 424/422 |
| 5,128,326 A | 7/1992 | Balazs et al. | 514/54 |
| 5,130,418 A | 7/1992 | Thompson | 530/399 |
| 5,143,662 A | 9/1992 | Chesterfield et al. | 264/8 |
| 5,158,934 A | 10/1992 | Ammann et al. | 514/12 |
| 5,202,311 A | 4/1993 | Folkman et al. | 514/12 |
| 5,206,023 A | 4/1993 | Hunziker | 424/423 |
| 5,217,954 A | 6/1993 | Foster et al. | 514/12 |
| 5,266,683 A | 11/1993 | Oppermann et al. | 530/326 |
| 5,294,446 A | 3/1994 | Schlameus et al. | 424/489 |
| 5,302,397 A | 4/1994 | Amsden et al. | 424/473 |
| 5,318,957 A | 6/1994 | Cid et al. | 514/8 |
| 5,344,644 A | 9/1994 | Igari et al. | 424/85.1 |
| 5,348,941 A | 9/1994 | Middaugh et al. | 514/12 |
| 5,354,557 A | 10/1994 | Oppermann et al. | 424/423 |
| 5,356,629 A | 10/1994 | Sander et al. | 424/422 |
| 5,366,505 A | 11/1994 | Farber | 623/11 |
| 5,366,964 A | 11/1994 | Lindstrom et al. | 514/57 |
| 5,368,858 A | 11/1994 | Hunziker | 424/423 |
| 5,368,859 A | 11/1994 | Dunn et al. | 424/426 |
| 5,387,673 A | 2/1995 | Seddon et al. | 530/399 |
| 5,399,352 A | 3/1995 | Hanson | 424/423 |
| 5,399,583 A | 3/1995 | Levy et al. | 514/410 |
| 5,409,896 A | 4/1995 | Ammann et al. | 514/13 |
| 5,416,071 A | 5/1995 | Igari et al. | 514/8 |
| 5,422,340 A | 6/1995 | Ammann et al. | 514/12 |
| 5,425,769 A | 6/1995 | Snyders, Jr. | 623/16 |
| 5,427,778 A | 6/1995 | Finkenaur et al. | 424/78.08 |
| 5,428,006 A | 6/1995 | Bechgaard et al. | 514/3 |
| 5,442,053 A | 8/1995 | della Valle et al. | 536/55.1 |
| 5,464,440 A | 11/1995 | Johansson | 623/11 |
| 5,470,829 A | * 11/1995 | Prisell et al. | 514/12 |
| 5,482,929 A | 1/1996 | Fukunaga et al. | 514/12 |
| 5,769,899 A | 6/1998 | Schwartz et al. | 623/18 |
| 6,005,161 A | * 12/1999 | Brekke et al. | 623/16 |

FOREIGN PATENT DOCUMENTS

WO    WO 91/15509    10/1991

OTHER PUBLICATIONS

Prisell et al. *Int. J. Pharmaceutics* 1992, 85, 51–56.*

Schiavinato et al., 1989, "Intraarticular Sodium Hyaluronate Injections in the Pond–Nuki Experimental Model of Osteoarthritis in Dogs," *Clinical Orthopedics and Related Research* 241:286–299.

Noda et al., 1994, "In Vivo Stimulation of bone formation by Transforming Growth Factor–β," *Endocrinolgy* 124:2991–4.

Pouyani and Prestwich, 1994, "Biotinylated Hyaluronic Acid: A New Tool for Probing Hyaluronate–Receptor Interactions," *Bioconjugate Chem.* 5:370–2.

A.A. Pilla, et al., "Non–Invasive Low–Intensity Pulsed Ultrasound Accelerates Bone Healing in the Rabbit", Journal of Orthopaedic Trauma, (1990) 4:246–253.

S. Jingushi, et al., "Acidic Fibroblast Growth Factor (aFGF) Injections Stimulates Cartilage Enlargement and Inhibits Cartilage Gene Expression in Rat Fracture Healing", Journal of Orthopaedic Trauma, (1990) 8:364–371.

Hiroshi Kawaguchi, et al., "Stimulation of Fracture Repair by Recombinant Human Basic Fibroblast Growth Factor in Normal and Streptozotocin–Diabetic Rats," Endocrinology, (1994)—135:774–781.

(List continued on next page.)

*Primary Examiner*—Kathleen K. Fonda
(74) *Attorney, Agent, or Firm*—Beyer Weaver & Thomas

(57) ABSTRACT

A composition is provided for treating diseased, injured or diseased cartilage comprising hyaluronic acid and a growth factor. The composition has a viscosity and biodegradability sufficient to persist at the site for a period of time sufficient to alleviate the symptoms of the disease, injury or abnormality. Preferably hyaluronic acid is used in a composition range of 0.01–4% by weight and the preferred growth factor is IGF-I, present in a concentration range of about $10^{-6}$ to 100 mg/ml.

14 Claims, No Drawings

OTHER PUBLICATIONS

Unworth, "Mechanics of Human Joints," pp. 137–162, Marcell Dekker, New York, 1993.
Meyer et al., Journal Biol. Chem. 107: 629–634, 1934.
Naoki et al., Journal Biol. Chem. 273: 1923–1932, 1998.
Laurent et al., Ann. Rheum, Dis., 54: 429–432, 1995.
Yelin et al., "Osteoarthritis", pp. 23–30, Oxford Univ. Press, N.Y., 1998.
Flores et al., "Osteoarthritis", pp. 1–12,Oxford Univ. Press, N.Y., 1998.
Lohmander et al., "Osteoarthritic Disorders," pp. 459–474, The Amer. Acad. Of Orthopedic Surgeons, Rosemond 1995.
Brandt et al., "Osteoarthritis" pp. 70–74, Oxford Univ. Press, N.Y., 1998.
Brandt, Rheum. Dis., North Am., 19: 697–712, 1993.
Ronziere et al., Biochem. Biophys. Acta, 1038: 222–230, 1990.
Eyre et al., "Articular Cartilage and Osteoarthitis", pp. 119–131, Raven press, N.Y., 1992.
Goetinck et al., J. Cell Biol., 105: 2403–2408, 1987.
Hascall et al., J. Biol. Chem., 249: 4232–4241, 1974.
Hacall, "Atlas of Science: Biochemistry," pp. 189–198, N.Y. 1988.
Torchia et al., J. Biol. Chem., 251: 3617–3625, 1977.
Handley, "Articular Cartilage and Osteoarthritis," pp. 411–413, Raven Press, N.Y. 1992.
McQuillan et al., Biochem. J., 240: 423–430, 1986.
Nissley et al., Arth. Biochem. Biophys., 267: 416–425, 1988.
Erlacher et al., Arthr. Rheum., 41: 263–273, 1998.
Benito et al., Int. J. Biochem. Cell Biol., 28: 499–510, 1996.
Luyten et al., Arth. Biochem. Biophys., 267: 416–425, 1988.
Middleton et al. Ann. Rheum. Dis., 51: 440–447, 1992.
Ng et al., Arth. Biochem. Biophys., 316: 596–606, 1995.
Tardif et al., Arth. Rheum., 39: 968–978, 1996.
Meyts et al., Horm. Res., 42: 152–169, 1994.
Keyszer et al., J. Rheumatol., 22: 275–281, 1995.
Rogachefsky et al., Osteoarthritis Cartilage, 1: 105–114, 1993.
Kubler and Urist, 1990, "Bone Morphogenetic Protein–Mediated Interaction of Periosteum and Diaphysis: Citric Acid and Other Factors Influencing the Generation of Parosteal Bone," *Clinical Orthopedics and Related Research* 258:279–294.

* cited by examiner

METHOD OF TREATING DISEASED, INJURED OR ABNORMAL CARTILAGE WITH HYALURONIC ACID AND GROWTH FACTORS

CROSS REFERENCE TO RELATED APPLICATIONS

This is a continuation-in-part of U.S. Ser. No. 08/811,971, filed Mar. 5, 1997, now U.S. Pat. No. 5,942,499, which is a continuation-in-part of Ser. No. 08/611,690, filed Mar. 5, 1996, now abandoned.

BACKGROUND OF THE INVENTION

Hyaluronic acid is a naturally-occurring polysaccharide containing alternating N-acetyl-D-glucosamine and D-glucuronic acid monosaccharide units linked with beta 1–4 bonds and the disaccharide units linked with beta 1–3 glycoside bonds. It occurs usually as the sodium salt and has a molecular weight range of about 50,000 to $8 \times 10^6$.

The joint cavity or synovium is filled with synovial fluid which is predominantly made up of hyaluronic acid (HA). The HA of the synovium is produced primarily by the synoviocytes that line the intima layer of the synovium, and proteins and nutrients that are drawn from the lymphatic system. The synovial fluid is a liquid form of an extracellular matrix that maintains the synovium volume and hydrostatic pressure, provides chondrocytes in the avascular particular cartilage with a steady flow of nutrients, lubricates the cartilage surface, and cushions the synovial tissue from the deforming forces of movements, (Unsworth, A., "Mechanics of Human Joints", (eds, Wright, V., and Radin, E. L.), pp 137–162, Marcel Dekker, New York, 1993). The rheological properties of synovial fluid are the result of the intricate meshwork of high molecular weight HA and its interaction with water molecules. It is a high molecular weight polymer made up of repeating disaccharide units of N-acetyl-glucosamine and glucuronic acid, Meyer, K., and Palmer, J. W., J. Biol. Chem. 107: 629–634, 1934.

The molecule is synthesized at the plasma membrane by the recently cloned hyaluronan synthase complex (Naoki, I., and Kimura, K., J. Biol. Chem., 271: 9875–9878, 1996 and Spicer, A. P. and McDonald, J. A., J. Biol. Chem., 273: 1923–1932, 1998). In a typically newly synthesized chain, upwards to 5000 disaccharide's units are present, though it is currently unclear how the newly synthesized chain lengths are determined. Hyaluronan turnover in normal human synovial fluid is estimated to be approximately 20 hours, (Laurent, T. C., Laurent, U. B. G., and Fraser, J. R. E., Ann. Rheum. Dis., 54: 429–432, 1995).

Osteoarthritis (OA) is a common joint disease of unknown etiology. The pathology of OA is characterized by a progressive loss of the particular cartilage of synovial joints with concomitant bony changes, including sclerosis and osteophyte formation (Yelin, E., "Osteoarthritis" (eds. Brandt, K., Doherty, M., and Lohmander, L. S.), pp. 23–30, Oxford University Press, New York, 1998; Flores, R. H., and Hochberg, M. C., "Osteoarthritis" (eds. Brandt, K., Doherty, M., and Lohmander, L. S.), pp. 1–12, Oxford University Press, New York, 1998). In some cases, hyperthrophy of the marginal and underlying bone, mild synovitis and capsular thickening are observed (Flores et al.). Initiation events for OA are unknown but recent findings indicate that the onset of this disease is highly dependent on the balance between mechanical stability of the joint and the degree of mechanical insult or injury. It has been postulated that mechanical instability of the joint will lead to a failure of the resident cartilage cells, known as chondrocytes, to maintain the balance between synthesis and degradation of the extracellular matrix. Ultimately, this homeostasis fails and the degradation process begins to outweigh new synthesis (Lohmander, L. S., "Osteoarthritic Disorders" (eds Kuettner, K. E., and Goldberg, V. M.), pp. 459–474, The American Academy of Orthopedic Surgeons, Rosemond 1995). The disease is particularly debilitating and disabling and is not easily treated at the time of detection. Early diagnosis is often difficult because of:

1) the lack of sensitive and cost permitting methods for early detection; and
2) the tendency of patients to attribute joint pain to the gradual but inevitable part of aging (Brandt, K., Lohmander, L. S., and Doherty, M., "Osteoarthritis" (eds. Brandt K., Doherty, M., and Lohmander, L. S.), pp. 70–74, Oxford University Press, New York, 1998). Consequently, this highly debilitating and degenerative disease is often not diagnosed until late stages of the disease that present clinical and radiographic manifestations. Current treatments or therapy are only palliative and designed to reduce pain and physical disability. Most medications that are in current use non-steroidal anti-inflammatory drugs (NSAIDs) which are often ineffective and in some instances have deleterious effects on cartilage metabolism (Brandt, K., D. Rheum. Dis., North Am., 19: 697–712, 1993). Most health care providers and afflicted patients are more interested in relieving the painful symptoms and disability associated with this disease. In view of a lack of curative treatment for OA, it is imperative that any current therapy being developed for this disease be aimed at relieving these debilitating and disabling symptoms.

The biochemistry and factors that regulate the metabolism of the joint, in particular particular cartilage, are a crucial part of the scientific rationale for designing a new treatment for OA. Particular cartilage is composed of an intricate collagenous scaffold that consists mainly of type II collagen, with types VI, XI and XI collagen found in specific locations throughout the matrix (Ronziere, M. C., Ricard-Blum, S., Tollier, J. et al, Biochim. Biophys. Acta, 1038: 222–230, 1990 and Eyre, D., Wu, J. J., and Woods, P., "Particular Cartilage and Osteoarthritis", (eds, Keuttner, K. E., Schleyerbach, R., Peyron, J. G., and Hascall, V. C.), pp. 119–131, Raven Press, New York, 1992). Within this matrix are found, large multi-ternary complexes, known as proteoglycan aggregates. These complexes are made up of an HA backbone and aggrecan molecules that interact specifically, in a non-covalent manner, via core protein sequences, that are also stabilized by a co-operative interaction with link protein (Goetinck, P. F., Stirpe, N. S., Tsonis, P. A., and Carlone, D., J. Cell Biol., 105: 2403–2408, 1987 and Hascall V. C., and Heinegard, D., J. Biol. Chem., 249: 4232–4241, 1974). The multiple glycosaminoglycan (GAG) chains on aggrecan are made up of mostly of chondroitin sulfate (approx. 100 chains of 15–20 kDa), and keratin sulfate (up to 50 chains of 5–8 kda) and confer the specialized viscoelastic and biomechanical properties of particular cartilage tissue (Hascall, V. C., "Atlas of Science: Biochemistry", (ed. Grimmwade), pp. 189–198, New York, 1988). As such, the concentration of GAGS and their anionic character, coupled with the integrity of the collagen meshwork, are the primary parameters that define the unique Theological properties of particular cartilage (Torchia, D. A., Hasson, M. A., and Hascall, V. C., J. Biol. Chem., 251: 3617–3625, 1977). It is, therefore, important that the metabolic regulation of these molecules by chondrocytes be maintained at a level that permits the tissue to function properly.

In normal cartilage, chondrocytes actively maintain a stable equilibrium between the synthesis and degradation of matrix components. In degenerative joint diseases like OA, this equilibrium is disrupted as the rate of proteoglycan and matrix loss begins to exceed the rate of deposition of newly synthesized molecules (Handley, C. J., "Particular Cartilage and Osteoarthritis", (eds, Keuttner, K. E., Schleyerbach, R., Peyron, J. G., and Hascall, V. C.), pp. 411–413, Raven Press, New York, 1992). Various factors are known to modulate and regulate proteoglycan aggregate complex metabolism in particular cartilage. Anabolic factors such as insulin-like growth factor-I (IGF-I) (Morales, T. I., and Hascall, V. C., Ann. Rheum., 32: 1197–1201, 1989; McQuillan, D. J., Handley, C. J., Campbell, M. A. et al., Biochem. J., 240: 423–430, 1986 and Luyten, F. P., Hascall, V. C., Nissley, S. P. et al., Arch. Biochem. Biophys., 267: 416–425, 1988, and growth differentiation factor-5 (GDF-5), Erlacher, L., Ng, C. K., Ullrich, R. et al., Arthr. Rheum., 41: 263–273, 1998), are of particular interest as specific mitogens that also promote the synthesis of proteoglycans and other matrix proteins in chondrocytes.

The IGFs are polypeptides that share structural and functional homology with insulin (Benito, M., Vlaverde, A. M., and Lorenzo, M., Int. J. Biochem. Cell Biol., 28: 499–510, 1996). In humans, two major IGFs isoforms are known; IGF-I (7.5 kDa) and IGF-II, that play a major part in the growth and development of many tissues during fetal and adult life. These factors are also implicated in tissue hyperthrophy and repair processes. IGF-I, a factor found in normal serum, is known to enhance the synthesis of collagen and proteoglycan in normal cartilage in vivo and in vitro (McQuillan, D. J., Handley, C. J., Campbell, M. A. et al., Biochem. J., 240: 423–430, 1986; Luyten, F. P., Hascall, V. C., Nissley, S. P. et al., Arch. Biochem. Biophys., 267: 416–425, 1988; Middleton, J. F. S., and Tyler, J. A., Ann. Rheum. Dis., 51: 440–447, 1992). Studies have shown that IGF-I increases the coordinated rate of proteoglycan, link protein and hyaluronan synthesis in adult particular cartilage explants (Luyten, F. P., Hascall, V. C., Nissley, S. P. et al., Arch. Biochem. Biophys., 267: 416–425, 1988 and Ng, C. K., Handley, C. J., Preston, B. N. et al., Arch. Biochem. Biophys., 316: 596–606, 1995).

Specific receptors for the IGF's have been detected in rabbit, bovine and human cartilage (Tardif, G., Reboul, P., Pelletier, J. P. et al., Arth. Rheum., 39: 968–978, 1996). So far, three structurally related receptors for members of this family have been identified: the insulin receptor, the type I IGF receptor, and an orphan receptor known only as insulin receptor-related receptor or IRR, (Meyts, P. D., Wallach, B., Christoffersen, C. T. et al., Horm. Res., 42: 152–169, 1994). These three receptors belong to the receptor protein tyrosine kinase family where they constitute a subgroup with distinct features and are encoded by a single gene located on human chromosomes 19, 15 and 1, respectively. The IGF-I receptor binds IGF-I with high affinity and IGF-II with an equally high or slightly lower affinity; it binds insulin with 500–1000 times lower affinity, explaining in part the well known role of insulin as a cartilage anabolic growth factor at high concentration.

There is evidence that the type I IGF receptor may play a role in the pathogenesis of OA (Keyszer, G. M., Heer, A. H., Kriegsmann, J. et al., J. Rheumatol., 22: 275–281, 1995). This was shown both in vitro, where IGF-I was found to reduce interleukin-1 (IL-l) stimulated cartilage degradation, and in vivo in an experimental model of OA in which IGF-I, administered in a combination with a synthetic protease inhibitor (sodium pentosan polysulfate (PPS), produced significant improvement in several OA disease parameters when compared with PPS or IGF-1 alone (Rogachefsky, R. A., Dean, D. D., Howell, D. S., and Altman, R. D., Osteoarthritis Cartilage, 1: 105–114, 1993).

SUMMARY OF THE INVENTION

The present invention provides a composition for treating diseased, injured or abnormal cartilage comprising hyaluronic acid and a growth factor such that the composition has a viscosity and biodegradability sufficient to persist at the site desired growth for a period of time sufficient to alleviate the symptoms of injury, disease or abnormality. The composition is also useful for treatment of diseased injured or abnormal osteochondral tissue, such as that found in osteoarthritis.

Viscosupplementation via the administration of hyaluronic acid (HA) into the damaged tissue, in combination with a cartilage anabolic growth factor, is a novel approach for alleviating the symptoms, inhibiting the further progression, and reversing the underlying pathophysiology of OA.

As used herein, the term hyaluronic acid, abbreviated as HA, means hyaluronic acid and its salts such as the sodium, potassium, magnesium, calcium, and the like, salts.

By growth factors, it is meant those factors, proteinaceous or otherwise, which are found to play a role in the induction or conduction of growth of ligaments, cartilage or other tissues associated with joints.

In particular these growth factors include bFGF, aFGF, EGF (epidermal growth factor), PDGF (platelet-derived growth factor), IGF (insulin-like growth factor), TGF-$\beta$ I through III, including the TGF-$\beta$ superfamily (BMP-1 through 12, GDF 1 through 8, dpp, 60A, BIP, OF).

DESCRIPTION OF THE PREFERRED EMBODIMENTS

The processes by which the compositions and the method of their use are described in more detail. The HA is preferably uncrosslinked having a molecular weight of 500,000 and above, typically in the range of $10^4$ to $10^7$ daltons. The cartilage growth-promoting compositions will typically contain from about 0.01 up to 4 percent by weight of uncrosslinked HA in an aqueous solution which also contains other solution excipients such as buffer salts, sugars, anti-oxidants and preservatives to maintain the solubility and bio-activity of the growth factor and proper pH of the composition. A composition containing from about 0.1 to 2 percent by weight of uncrosslinked HA is preferred. A typical pH of the solution will be in the range of 4 to 9, preferably about 6.0±1.0 and most preferably about 5.0.

Several HA preparations with different molecular weights are readily available. The molecular weight ranges of commercially available HA vary from $8 \times 10^5 - 7 \times 10^6$ Da ($8 \times 10^5$ Da for Artz®, Seikagaku Kogyo, Co. Ltd. and Hyalgan®, Fidia Co. Ltd., $7 \times 10^6$ Da for Synvisc®, Biomatrix Co. Ltd.). Typically, studies are conducted with HA purified from rooster comb, such as, HA in the range of $1-3 \times 10^6$ Da (Anika Therapeutics, MA).

The growth factor will typically be present in the solution in a concentration range of about $10^{-6}$ to 100 mg/ml of solution, and particularly in the case of the IGF family of proteins or their active fragments, about 0.1 to 20 mg/ml. The concentration will be dependent upon the particular site and application, as well as the volume of the injection and specific activity of the growth factor. The preferred growth factor is IGF-I.

The utility of HA stems from the synergistic interaction with active agents that:
1) localizes and sustains the active agent at the site of injection, and;
2) increases the stability of the biologically active agents. The combination of HA with a cartilage specific anabolic factor provides not only a symptomatic relief, but also an inhibition of progression of the underlying pathophysiology of OA;
3) provide their own benefit in the treatment of OA;
4) Utilize similar and overlapping intracellular signalling pathways to facilitate a biologic response.

It is important for the solution to have a viscosity which allows it to be injectable through a syringe or catheter, but not to be prematurely diluted by the body fluids before the desired effect can be achieved. Preferably, the viscosity of the composition is within a range of 10 to $10^6$ cP and, in the case of IFG-I containing compositions, preferably about 75,000 cP.

It is also important for the composition to have a biodegradability which is sufficient to allow it to remain in place at the site of diseased, injured or abnormal cartilage to effect the symptom alleviating activity.

The composition must usually persist at the particular site for a period from about three (3) to about thirty (30) days, typically from three (3) to about fourteen (14) days.

The compositions are typically formed as solutions by mixing the HA and growth factor in appropriate amounts of excipients such as sodium citrate, EDTA and sucrose so that the HA and growth factor remain in solution at the desired concentration and the solution exhibits the appropriate viscosity and biodegradability. The composition may also contain growth factor binding proteins, such as an IGF-I binding protein, which prolong the period of activity of the growth factor at the site of application. The solution may be applied to an particular site in any convenient manner, typically by introduction through a syringe or catheter.

Administration of a composition of the present invention may be desirable to accelerate healing, prevent further tissue damage from occurring subsequent to injury, avoid treatments that compromise the natural healing process and create optimal physical and biological conditions for healing. Typical particular sites include vertebral compression injuries, rib injuries and joint injuries. Effective dosages are typically about $10^{-3}$ to $10^{-4}$ µg/kg of body weight of compositions containing about 0.01–4% by weight HA and about $10^{-6}$ to 100 mg/ml of growth factor. The invention is described in more detail in the following examples, which are provided by way of illustration and are not intended to limit the invention set forth in the claims.

EXAMPLE

This is an evaluation of the effect of the injection of hyaluronate combined with IGF-I in rabbits using an experimental model of early stages of osteoarthritis induced by transection of the anterior cruciate ligament:

Test Materials

The hyaluronate/IGF-I formulation was prepared aseptically by mixing a sterile solution of IGF-I (100 @ ml) prepared in 20 mM sodium citrate; 9% sucrose, 1 mM EDTA; pH=4.5 with lyophilized sodium hyaluronan (20 mg/ml) to complete dissolution and homogeneity. Sodium hyaluronan was obtained by Anika Therapeutics (Woburn, Mass.) as ethanol precipitate. Recombinant human IGF-I was purchased from R&D System (Minneapolis, Minn.).

The effect of sodium hyaluronate/IGF-I injection on damaged cartilage in an osteoarthritic knee joint was evaluated in rabbits using an experimental model of osteoarthritis induced by sectioning the anterior cruciate ligament. Efficacy was measured based on an assessment of gross morphology (Table I) and inflammation (Table II). The rheological efficacy of HA/IGF-I combination was compared to injection of hyaluronan (current standard clinical practice) or vehicle alone.

New Zealand White rabbits at least 1 year of age with closed epiphyses was used in the feasibility study. The experimental design is summarized in Table III. All rabbits were undergone unilateral anterior cruciate ligament transection (ACLT) and divided into four groups. The contralateral nonoperated knee served as paired controls. The first group (control) (A) undergone unilateral ACLT but received no injection. The second group (vehicle) (B) received buffer solution 4 weeks after ACLT, once a week for 5 weeks. Similarly, the third group (hyaluronan) (C) received injections of HA alone, the fourth group received injection of hyaluronan and IGF-I (0.2 mg/ml) (D), once a week for 5 weeks. Animals were sacrificed one week after the fifth and final injection. The joints were analyzed by gross morphology assessment (Table I), and evaluation of swelling (Table II).

Gross Morphological Assessments

The femoral condyle and tibial plateaus were photographed using a 35 mM camera (Yashica, Japan) equipped with a close up micro lens. Gross morphological changes of the femoral condyles and tibial plateaus were assessed according to the criteria shown in Table I following the application of India ink. As summarized in Table IV, the hyaluronan injection appeared to have a chondroprotective effect on the degradation of the particular cartilage following ACLT as compared to Vehicle or controls consistent with previous findings (1). However, under these experimental conditions, HA/IGF-I formulation suppressed or delayed the progression of osteoarthritis more significantly than HA injection alone (the current standard clinical practice). Furthermore, as shown in Table V, neither HA/IGF-I nor HA injection did significantly increase the swelling induced by this animal model.

The results thus indicate that the HA/IGF-I combination presented a superior cartilage protective effect as compared to the HA injection (the current standard clinical practice) as measured by gross morphological assessments. See Shimizu et al., and Rydell et al., cited below Table V.

TABLE I

Criteria used for gross morphological assessments:

| Grade 1 | Intact surface | No India ink retained |
|---|---|---|
| Grade 2 | Minimal fibrillation | Ink retained as elongated specks or light grey patches |
| Grade 3 | Overt fibrillation | Ink retained as intense black patches, velvety in appearance |
| Grade 4 | Erosion | Loss of cartilage exposing the underlying bone |
| Grade 4a | 0 mm < erosion < 2 mm | |
| Grade 4b | 2 mm < erosion < 5 mm | |
| Grade 4c | 5 mm < erosion | |

TABLE II

Grading used for assessment of joint swelling:

| Grade 0 | Normal | — |
|---|---|---|
| Grade +1 | Mild | Inflammation and/or proliferation of the joint capsule |
| Grade +2 | Moderate | Thickening of joint capsule and/or inflammatory synovium |
| Grade +3 | Severe | Abundant inflammatory synovium; swelling of menisci or ligament |

TABLE III

Study for evaluation of the rheological efficacy of administering hyaluronan in combination with IGF-I.

| | Number of animals per experimental condition* |
|---|---|
| Control (A) | 5 |
| Vehicle (B) | 10 |
| Hyaluronan (C) | 10 |
| Hyaluronan + IGF-I (D) | 10 |

*Histomorphometric analysis of different injectable formulation will be assessed based on gross morphology (see Table I).

TABLE IV

Summary of Gross Morphological Assessment:

| | A (N = 5) | B (N = 10) | C (N = 9) | D (N = 10) |
|---|---|---|---|---|
| Femur | | | | |
| Grade 1 | 1 | 2 | 0 | 4 |
| Grade 2 | 2 | 2 | 4 | 4 |
| Grade 3 | 0 | 2 | 2 | 1 |
| Grade 4a | 0 | 3 | 1 | 0 |
| Grade 4b | 2 | 1 | 1 | 0 |
| Grade 4c | 0 | 0 | 1 | 1 |
| Tibia | | | | |
| Grade 1 | 1 | 1 | 0 | 3 |
| Grade 2 | 1 | 4 | 5 | 5 |
| Grade 3 | 1 | 2 | 3 | 1 |
| Grade 4a | 1 | 2 | 1 | 1 |
| Grade 4b | 1 | 2 | 0 | 0 |
| Grade 4c | 0 | 0 | 0 | 0 |

TABLE V

Summary of swelling grading of inflammatory response:

| Swelling | A (N = 5) | B (N = 10) | C (N = 9) | D (N = 10) |
|---|---|---|---|---|
| 0+ | 1 | 2 | 0 | 1 |
| 1+ | 1 | 4 | 6 | 4 |
| 2+ | 3 | 4 | 3 | 5 |
| 3+ | 0 | 0 | 0 | 0 |

1) Shimizu C., Kubo, T., Hirasawa, Y., Coutts, R. D., and Amiel D. Histomorphometric and Biochemical Effect of Various Hyaluronans on Raely Osteoarthritis. J. of Rheumatology 1998; 25: 1813–1819.

2) Rydell, N. W., Butler, J., Balazs, E. A. Hyaluronic acid in synovial fluid; Effect of intra-particular injection of hyaluronic acid on the clinical symptoms of arthritis in track horses. Acta Vet Stand 1970; 11: 139–55.

The foregoing disclosure and description of the invention are illustrative and explanatory thereof and various changes in the size, shape and materials as well as in the details of the preferred embodiment may be made without departing from the spirit of the invention.

What is claimed is:

1. A method of treating diseased, injured or abnormal cartilage comprising the step of applying to a site of diseased, injured or abnormal cartilage a liquid composition comprising an effective amount of a mixture of hyaluronic acid and a growth factor sufficient to alleviate the symptoms of the disease, injury or abnormality, wherein said composition has a viscosity and biodegradability sufficient to persist at said site for a period of time sufficient to alleviate said symptoms.

2. A method according to claim 1 wherein said hyaluronic acid is uncrosslinked.

3. A method according to claim 1 wherein said hyaluronic acid in said composition comprises about 0.01–4% by weight of said composition.

4. A method according to claim 1 wherein said growth factor comprises a member of the IFG family of proteins, active proteins fragments thereof.

5. A method according to claim 4 wherein said composition further comprises a growth factor binding protein.

6. A method according to claim 4 wherein said growth factor comprises IGF-I.

7. A method according to claim 6 wherein said composition further comprises an IGF-I binding protein.

8. A method according to claim 6 wherein said IFG-I is present in a range of about $10^{-6}$ to 100 mg/ml in said composition.

9. A method according to claim 1 wherein said effective amount is in the range of $10^{-3}$ to $10^{-4}$ μg/kg body weight.

10. A method according to claim 1 wherein said site is an osteoarthritic joint.

11. A method according to claim 1, wherein applying the composition comprises applying to the diseased, injured or abnormal cartilage a liquid composition consisting of an aqueous mixture of hyaluronic acid, a growth factor and one or more excipients.

12. A method according to claim 11, wherein the one or more excipients are selected from the group consisting of buffer salts, sugars, antioxidants and preservatives.

13. A method according to claim 11, wherein upon application of the composition to the site of diseased, injured or abnormal cartilage, the pH at the site is maintained at an acidic pH in the range of 4–9.

14. A method according to claim 13, wherein upon application of the composition to the site of diseased, injured or abnormal cartilage, the pH at the site is maintained at a pH of about 5.0.

* * * * *